United States Patent [19]

Wu

[11] 4,170,996
[45] Oct. 16, 1979

[54] CATHETERIZATION UNIT

[75] Inventor: Yeongchi Wu, Darien, Ill.

[73] Assignee: Rehabilitation Institute of Chicago, Chicago, Ill.

[21] Appl. No.: 848,005

[22] Filed: Nov. 3, 1977

[51] Int. Cl.$^2$ ............................................ A61M 25/00
[52] U.S. Cl. ................................................ 128/349 R
[58] Field of Search ........ 128/349 R, 349 B, 349 BV, 128/348, 350 R, 351, 214.4, DIG. 9

[56] References Cited

U.S. PATENT DOCUMENTS

| | | | |
|---|---|---|---|
| 3,050,066 | 8/1962 | Koehn | 128/349 B |
| 3,421,509 | 1/1969 | Fiore | 128/349 R |
| 3,444,860 | 5/1969 | Harrell | 128/349 R |
| 3,515,137 | 6/1970 | Santomieri | 128/214.4 |
| 3,556,294 | 1/1971 | Walck | 128/349 R X |
| 3,592,192 | 7/1971 | Harautuneian | 128/348 |
| 3,854,483 | 12/1974 | Powers | 128/349 R |
| 3,894,540 | 7/1975 | Bonner, Jr. | 128/349 R |
| 3,898,993 | 8/1975 | Taniguchi | 128/349 R |
| 4,062,363 | 12/1977 | Bonner, Jr. | 128/349 R |

FOREIGN PATENT DOCUMENTS

| | | | |
|---|---|---|---|
| 1170586 | 5/1964 | Fed. Rep. of Germany | 128/DIG. 9 |
| 1174397 | 12/1969 | United Kingdom | 128/349 R |

*Primary Examiner*—E. H. Eickholt
*Attorney, Agent, or Firm*—Trexler, Wolters, Bushnell & Fosse, Ltd.

[57] ABSTRACT

A reuseable catheterization unit, including a catheter member of a predetermined diameter, a hollow flexible sleeve means connected at one end to the large diameter portion of the catheter and a hollow tubular connector means positioned at the opposite end of the sleeve means and axially spaced from the anterior end of the catheter, said connector mean adapted to sealingly connect with the large tubular end of the catheter to form a closed ring capable of sealingly retaining an antiseptic fluid within the lumen of the sleeve as well as contacting the exterior and lumen of the catheter for aseptic storage between catheterization procedures.

8 Claims, 6 Drawing Figures

U.S. Patent  Oct. 16, 1979  4,170,996
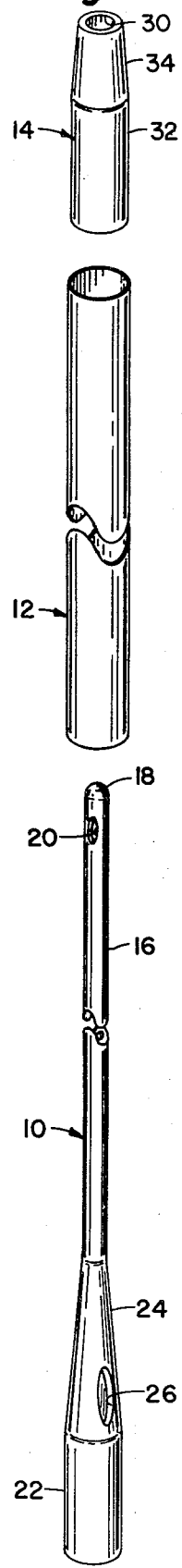
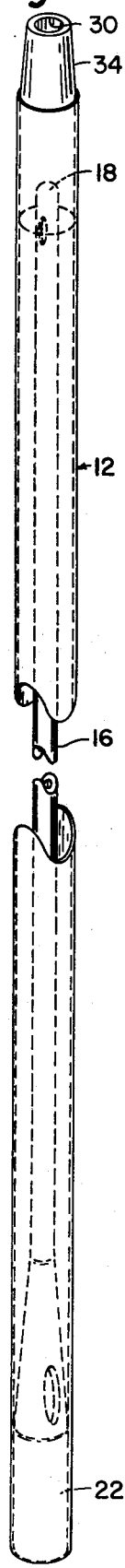
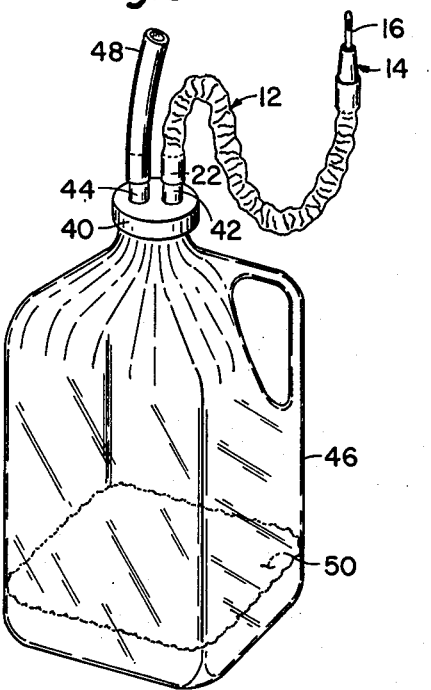
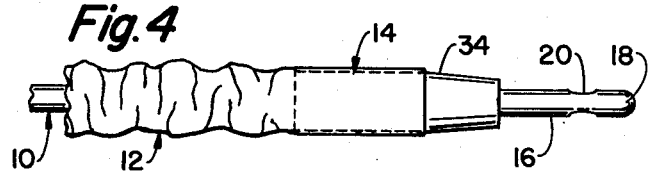
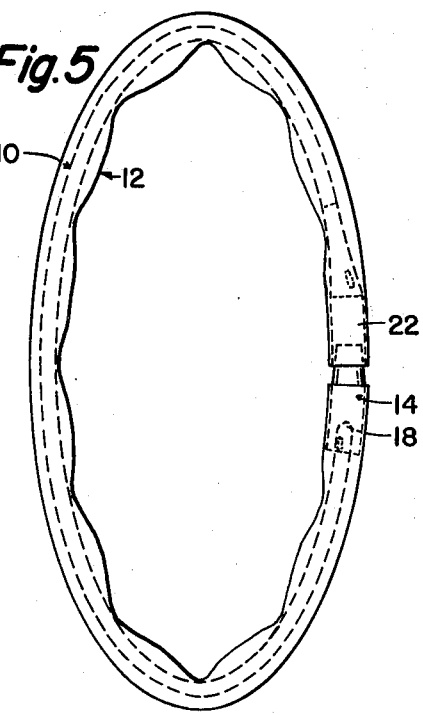
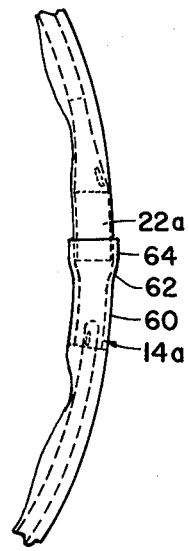

2

CATHETERIZATION UNIT

BACKGROUND OF THE INVENTION

The use of catheter devices having an elongated tubular member provided with a closed anterior end and side ports spaced from said closed end communicating with the lumen of a catheter for introduction into the urethral passageway for draining of a bladder when the ports reach the interior of the bladder is well known in the art. Such catheters are used in hospitals, clinics and homes under aseptic conditions for either continuous or intermittent catheterization of patients who suffer from neurogenic bladders, i.e. paraplegics and quadraplegics, and who are unable to evacuate their fluid waste materials. Such procedures, however, generally have been felt to require aseptic conditions to prevent secondary infections of the urethral passageway and bladder. It will be recognized that the requirement of aseptic conditions in institutions normally includes a high labor cost for professional personnel, i.e. doctors and nurses, plus in institutional or home use the cost of an expensive "tray" kit of drapes, gloves, tongs, catheter, etc., and hence produces excessive costs to the patient. Basically, the reason for such requirement of aseptic conditions is the fact that the catheter, which is to be inserted into the urethral passageway and bladder, is totally exposed to the surrounding environment and hence its external surfaces, in order to maintain sterility must be handled as if it is being used in a surgical procedure and environment.

SUMMARY OF THE INVENTION

The present invention relates to a catheter unit in which the catheter per se, including all portions, is to be inserted within the urethral passageway and is initially encased in an elongated sleeve and provided with a connector member which is fastened to the sleeve at one end while the opposite end of the sleeve is connected to the enlarged distal end of the catheter. The connector means is capable of being sealingly connected through cooperative means to said enlarged end of the catheter whereby the enclosed catheter can be subjected to an antiseptic fluid for maintaining sterility prior to use and which fluid is disposed of prior to use. The sleeve being a flexible member can be moved axially along relative to said catheter to expose same for introduction into the urethral passageway. After use and evacuation through the distal end of the catheter into a suitable container, i.e. a vented bottle, toilet or bidet, the sleeve can then be extended to once again encircle the catheter, an antiseptic fluid poured into the lumen of the sleeve and catheter and the unit prepared for later useage.

Because of the total encapsulation of the catheter, the unit contemplated by this invention can be utilized in a "clean" environment where simple "scrubbing" techniques, rather than aspetic techniques, may be used. Thus, this unit, while reuseable, provides a dramatic reduction in cost of use.

A further object of the present invention is to provide an economical reuseable clean catheter which can be employed by appropriate parties in a nonsterile environment.

Other objects will be apparent to those skilled in the art.

BRIEF DESCRIPTION OF THE DRAWINGS

FIG. 1 is an exploded view in perspective of the elements contemplated by the present invention;

FIG. 2 is a perspective broken view of the elements making up a catheter unit contemplated by the present invention in assembled relation;

FIG. 3 is a perspective view of the embodiment of the present invention as connected to a container for receiving evacuated body waste fluids;

FIG. 4 is a partial side elevational view of an embodiment of the present invention showing it in the initial stages of introduction;

FIG. 5 is a plan view of the present invention in connected sealing arrangement in a ring configuration; and FIG. 6 is a partial side elevational view of a secondary form of connector means.

DETAILED DESCRIPTION

Referring now to the drawings wherein similar parts are designated by similar numerals, a reuseable urethral intermittent catheter unit of the type contemplated by the present invention includes a urethral catheter 10, a thin wall flexible sleeve 12 and a connector element 14. The catheter is a type that is commercially available and includes an elongated hollow portion 16 having a closed end 18 and one or more side ports 20 that communicate through the side wall to the interior lumen at a point adjacent the closed end 18. At the distal end of the catheter there is an enlarged substantially cylindrical portion 22 connected to the balance of the catheter by a tapered portion 24. The enlarged end 22 is open and provides egress for all fluid collected through the ports 20. Normally, the elongated portion 16 and the closed end 18 are suitably lubricated, as is well known, prior to introduction into the urethral passageway of a patient. Additionally, in this embodiment the tapered portion 24 includes one or more port means 26, for purposes best set forth hereinafter. Such catheters normally are fabricated from rubber or a similar material to provide the necessary flexibility.

A flexible sleeve 12 that can be fabricated from "penrose" draining tube which is a thin wall laytex like material or from any other suitable flexible thin wall material such as polyethylene or other plastic materials is provided. The sleeve 12 is fastened adjacent the distal end of the enlarged portion 22 by suitable means such as adhesive, heat or sonic welding. At the opposite end a connector means 14 is inserted into the sleeve 12 and includes a through bore 30 that has a diameter in excess of the predetermined diameter of elongated portion 16 of the catheter. The connector element 14, in this embodiment, includes a cylindrical portion 32 and a tapered portion 34 with the sleeve 12 being connected to the cylindrical portion 32.

Referring now to FIGS. 3 and 4, a catheter unit of this type is utilized by compressing the walls of sleeve 12 to grasp the catheter, and by manipulation axially moving the connector 14 axially relative to the catheter, thereby wrinkling or corrugating the flexible sleeve 12 to expose the closed end 18 of the catheter and its adjacent ports 20. The tapered end 34 of the connector is positioned adjacent the external opening of the urethra and by axial movement along the catheter 16 permits introduction of the closed end 18 into the urethral passageway. The sleeve 12 and connector 14 are moved axially relative to the catheter 16 as it is inserted deeper and deeper into the urethral passageway until the ports 20 communicating with the lumen of the catheter reaches the interior of the bladder and evacuation of body waste fluids commences.

As the sleeve 12 is collapsed axially in a wrinkled or corrugated fashion so that the mast of the sleeve is then adjacent the enlarged end 22, it has been found desirable to provide ports 26 in the tapered portion 24 to allow entrapped air within the lumen of the sleeve to be evacuated through the distal enlarged end 22 of the catheter 10. The waste body fluids are evacuated freely through the enlarged end 22 into a toilet, a bidet or, if desire, into a vented container such as shown in FIG. 3. The container in FIG. 3 is a standard plastic milk bottle having a cap 40 with a pair of tubular stub means 42 and 44 communicating through the cap 40 to the interior of the container 46. The enlarged distal end 22 can be accepted over stub means 42 and a suitable vent pipe 48 extends upwardly from the tube 44 to prevent spillage. If desired, a small amount of fluid 50 containing an acetic solution to prevent odors can be utilized.

Due to the paralyzed condition of most patients using this catheter, withdrawal of the unit from the urethral passageway will automatically result in cessation of fluid flow. The container can then be evacuated, the catheter and its sleeve rinsed off and a fresh measure of antiseptic reintroduced into the lumen of the catheter and sleeve by pouring the solution into the enlarged end 22 of the catheter. The tapered end 34 of connector 14 is then introduced into the lumen of an enlarged end 22 and having a tapered fit will seal the device into a circle formation, as seen in FIG. 5. When the next intermittent catheterization is desired, the unit is opened into elongated form, the antiseptic solution drained from the unit by holding the connector 14 in a lower position than other portions of the catheter to thereby drain both the lumen of the catheter as well as the lumen of the sleeve 12 for immediate reuseage as previously described.

It will be recognized that many other forms of sealing connecting means can be utilized. For example, as seen in FIG. 6, the connector 14a includes a cylindrical portion 60, a tapered intermediate portion 62 and an enlarged end 64 capable of accepting the distal end 22a of the catheter internally thereof. Other connecting arrangements to sealingly form the circle described will be apparent to those skilled in the art.

It has been found that a F14–16 straight catheter that is commercially available will utilize from 5 to 10 cc of Betadine solution for sterilization purposes. This type of solution also has the added advantage of serving as a lubricant for the external surfaces of the elongated portions 16 of catheter 10.

I claim:

1. A reuseable catheter unit including a catheter member of a predetermined diameter through a substantial part of its extent and having a closed anterior end, at least one side port adjacent said anterior end which communicates with a lumen passing through the remainder of said catheter member, an enlarged distal end having a large diameter portion connected by a tapered wall portion to the predetermined catheter member diameter, aperture means on said tapered wall portion communicating between the interior and exterior of said tapered wall portion, flexible sleeve means connected at one end to said large diameter portion and encasing said catheter member throughout all of its length and hollow tubular connector means positioned at the opposite end of said sleeve means, said tubular connector means axially spaced from the anterior end of said catheter member and further including a bore greater than said predetermined diameter, said connector means and said enlarged distal end of the catheter member having cooperative means for sealingly connecting to one another when said sleeve and the catheter member contained therein are formed into a circle thereby forming a closed ring capable of sealingly retaining an antiseptic fluid within the lumen of the sleeve and the exterior and lumen of said catheter member for aseptic storage between catheterization procedures.

2. A unit of the type claimed in claim 1 wherein said tubular connector means is tapered at its free end opposite the end connected to said sleeve means and said free end is acceptable within said large diameter portion at the distal end of the catheter in sealing engagement.

3. A unit of the type claimed in claim 1 wherein the tubular connector means encircles and overlies the large diameter of the distal end of the catheter member in sealing arrangement.

4. A unit of the type claimed in claim 1 wherein said sleeve means is a thin wall rubber tube capable of being axially corrugated to feed the catheter member out through the bore of the tubular connector means.

5. A unit of the type claimed in claim 1 wherein said sleeve is a flexible plastic sheath capable of being corrugated during the axial movement of the tubular connector means relative to the catheter member.

6. A unit of the type claimed in claim 4 wherein said rubber tube is adhesively connected to the tubular connector means at one end and adhesively connected to the enlarged distal end of the catheter member.

7. A unit of the type claimed in claim 1 wherein said apertured means on said tapered wall portion communicates between the lumen of the catheter member and the lumen of the sleeve means whereby air within the sleeve means can be evacuated out the enlarged distal end of the catheter member as said sleeve means is axially moved and corrugated during feeding of the catheter member through the tubular connector means.

8. A unit of the type claimed in claim 1 wherein said enlarged distal end of the catheter member is capable of being connected to a vented container for receiving a urine sample during catheterization procedures.

* * * * *